US011633371B2

(12) United States Patent
Sippy

(10) Patent No.: US 11,633,371 B2
(45) Date of Patent: *Apr. 25, 2023

(54) DEUTERATED FORMS OF ACETAMINOPHEN AND USES THEREOF

(71) Applicant: Lennham Pharmaceuticals, Inc., Concord, MA (US)

(72) Inventor: Bradford C. Sippy, Acton, MA (US)

(73) Assignee: Lennham Pharmaceuticals, Inc., Concord, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/667,465

(22) Filed: Feb. 8, 2022

(65) Prior Publication Data

US 2022/0160660 A1 May 26, 2022

Related U.S. Application Data

(63) Continuation of application No. 17/616,383, filed as application No. PCT/US2020/035866 on Jun. 3, 2020.

(60) Provisional application No. 62/861,073, filed on Jun. 13, 2019, provisional application No. 62/857,226, filed on Jun. 4, 2019.

(51) Int. Cl.
*A61K 31/167* (2006.01)
*A61P 1/16* (2006.01)
*A61K 31/522* (2006.01)
*A61K 45/06* (2006.01)
*A61P 29/00* (2006.01)

(52) U.S. Cl.
CPC .......... *A61K 31/167* (2013.01); *A61K 31/522* (2013.01); *A61K 45/06* (2013.01); *A61P 1/16* (2018.01); *A61P 29/00* (2018.01)

(58) Field of Classification Search
CPC ........ A61K 31/167; A61K 31/592; A61P 1/16
See application file for complete search history.

(56) References Cited

U.S. PATENT DOCUMENTS

2014/0243407 A1* 8/2014 Bley .................. A61P 1/04
560/163

OTHER PUBLICATIONS

Kaur et al. "Deuteration as a tool for optimization of metabolic stability and toxicity of drugs," Global J. Pharmacy & Pharmaceutical Science, 2017, vol. 1, No. 4, ID 555566, https://juniperpublishers.com/gjpps/pdf/GJPPS.MS.ID.555566.pdf (Year: 2017).*
Tsikas et al. ("In-source formation of N-acetyl-p-benzoquinone imine (NAPQI), the putatively toxic acetaminophen (paracetamol) metabolite, after derivatization with pentafluorobenzyl bromide and GC-ECNICI-MS analysis," J. Chromatography B, 2011, vol. 879, pp. 1476-1484) (Year: 2011).*
PubChem CID12983636 (Year: 2017).*
(Continued)

*Primary Examiner* — Shengjun Wang
(74) *Attorney, Agent, or Firm* — Wolf, Greenfield & Sacks, P.C.

(57) ABSTRACT

The present disclosure provides compositions comprising deuterated forms of acetaminophen. When administered to human subjects, such compositions form less of the toxic metabolite NAPQI, and therefore are useful in methods of treating various diseases and conditions with a reduced risk of liver injury or other side effects associated with non-deuterated forms of acetaminophen.

28 Claims, 1 Drawing Sheet

(56) References Cited

OTHER PUBLICATIONS

PubChem CID 12205927 (Year: 2007).*
PubChem CID 131869277 (Year: 2017).*
U.S. Appl. No. 17/616,383, filed Dec. 3, 2021, Sippy.
International Search Report and Written Opinion for PCT/US2020/035866 dated Oct. 6, 2020.
International Preliminary Report on Patentability for PCT/US2020/035866 dated Dec. 16, 2021.
Lukin et al., Isotope Labeling Reveals Fast Atomic and Molecular Exchange in Mechanochemical Milling Reactions. J Am Chem Soc. Jan. 23, 2019; 141(3):1212-1216. doi: 10.1021/jacs.8b12149. Epub Jan. 9, 2019. PMID: 30608669.
Harbeson et al., Deuterium in Drug Discovery and Development. Annual Reports Med Chem. 2011;46:403-417.
Shao et al., Derivatives of tramadol for increased duration of effect. Bioorg Med Chem Lett. Feb. 2006;16(3):691-4. doi: 10.1016/j.bmcl.2005.10.024. Epub Oct. 27, 2005. PMID: 16257206.

* cited by examiner

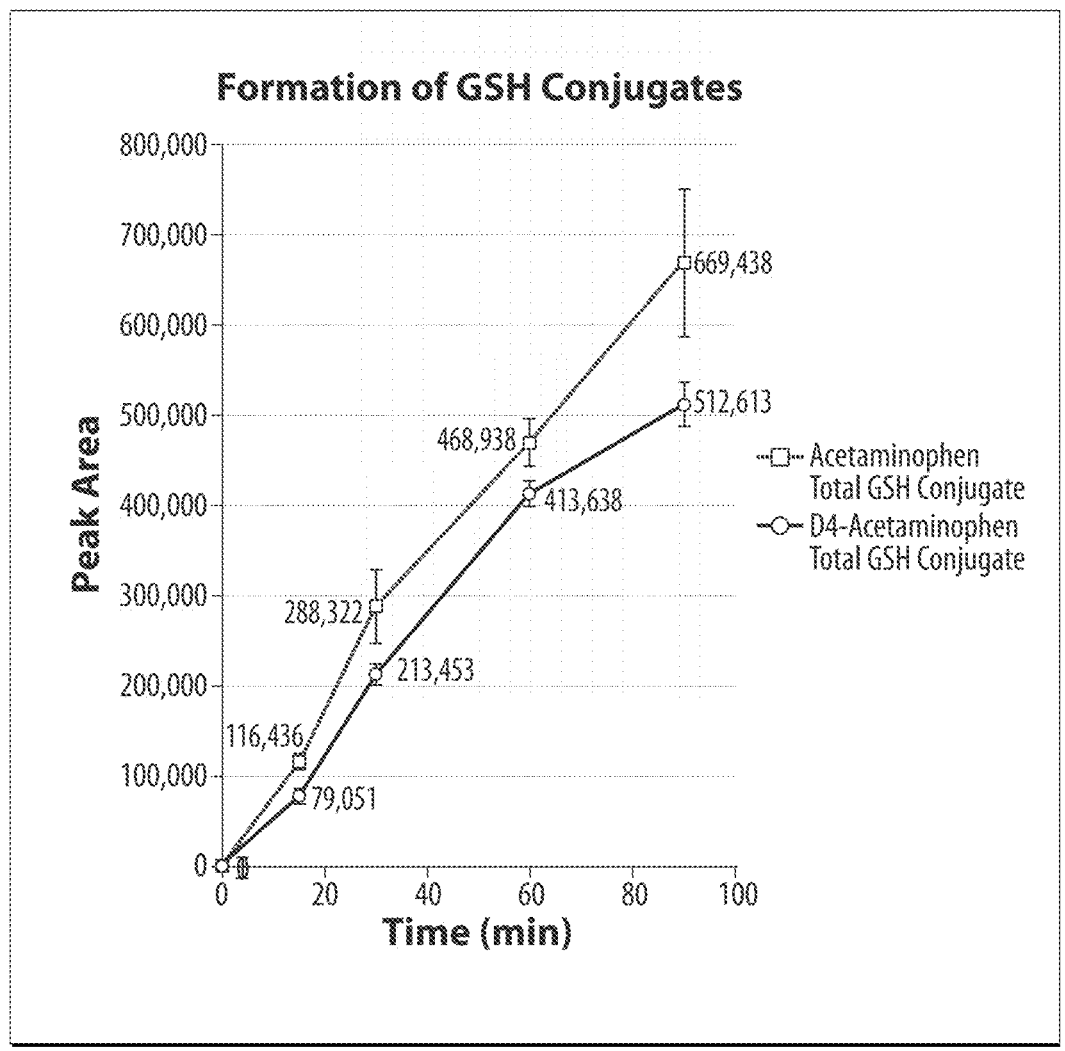

DEUTERATED FORMS OF ACETAMINOPHEN AND USES THEREOF

CROSS REFERENCE TO RELATED APPLICATIONS

The present application is a continuation of and claims priority under 35 U.S.C. § 120 to U.S. patent application Ser. No. 17/616,383, filed Dec. 3, 2021, which is a national stage filing under 35 U.S.C. § 371 of International PCT Application PCT/US2020/035866, filed Jun. 3, 2020, which claims priority under 35 U.S.C. § 119(e) to U.S. Provisional Application No. 62/861,073, filed on Jun. 13, 2019, and U.S. Provisional Application No. 62/857,226, filed on Jun. 4, 2019, the entire contents of which are herein incorporated by reference.

BACKGROUND OF THE INVENTION

Acetaminophen (also known as paracetamol) was approved by the FDA in 1951 and is one of the most widely used drugs in the United States. Today, acetaminophen is found in hundreds of over-the-counter (OTC) and prescription medicines, including in Tylenol-brand products, as an intravenous formulation (OFIRMEV), and in prescription combination drug products such as Vicodin and Percocet.

The chemical structure of acetaminophen, N-(4-Hydroxyphenyl)acetamide, is as follows:

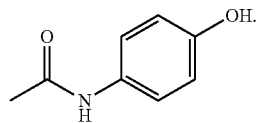

Acetaminophen is a pain reliever and fever reducer that is used to treat many conditions including headaches, muscle aches, arthritis, backache, toothaches, colds, and fevers (including hemorrhagic fevers). Acetaminophen is also combined with other active ingredients to treat conditions such as allergy, cough, colds, flu, and sleeplessness.

Acetaminophen is metabolized by the liver and is thought to function by reducing the levels of prostaglandins in the brain. Acetaminophen is not part of the non-steroidal anti-inflammatory or "NSAID" family of drugs, such as ibuprofen or naproxen.

Despite its widespread use, acetaminophen has been known for years to cause liver injury. Because of that, in 2007, the FDA convened a working group to discuss medical data and regulatory options for prescription and over-the-counter (OTC) acetaminophen products. In 2011, the FDA adopted measures recommended by an FDA advisory committee to reduce the risk of severe livery injury associated with acetaminophen, including limiting the acetaminophen content in prescription combination products to 325 mg per dosage unit; and requiring a "black box" warning on all prescription acetaminophen products to alert health care providers and patients of the risk of severe livery injury.

Notwithstanding the FDA's actions, acetaminophen overdose remains a significant problem, as it is the leading cause of acute liver failure in the United States. The hepatotoxicity of acetaminophen is thought to be due to the production of the reactive metabolite N-acetyl-p-benzoquinone imine ("NAPQI"). NAPQI detoxification occurs primarily by glutathione (GSH) conjugation. After GSH depletion, however, NAPQI is thought to form adducts with cellular proteins (macromolecules) that then initiate mitochondrial dysfunction and, subsequently, hepatocyte necrosis. See Ramachandran et al. "Mitochondrial dysfunction as a mechanism of drug-induced hepatotoxicity: current understanding and future perspectives." *Journal of Clinical and Translational Research*, vol. 4,1 (2018). As a result, the maximum recommended daily dose of acetaminophen in adults is 4,000 mg.

Despite being on the market for more than sixty (60) years, scientists have been unsuccessful in developing and commercializing a safer, improved form of acetaminophen. Unfortunately, alternatives to acetaminophen, such as NSAIDs and opioids, come with different, but serious, and in many cases life threatening, risks. For example, NSAIDs, such as ibuprofen, today carry a "black box" warning of (a) an increased risk of serious cardiovascular thrombotic events, myocardial infarction, and stroke, and (b) an increased risk of serious gastrointestinal adverse events including bleeding, ulceration, and perforation of the stomach or intestines, both of which may be fatal. Opioids, on the other hand, are widely known to lead to addiction, abuse, and misuse, which can result in overdose and death. As such, there is a need for safe and effective alternatives to existing pain relievers and fever reducers such as acetaminophen.

SUMMARY OF THE INVENTION

Described herein is an invention that solves the significant, long felt need for safe and effective non-NSAID, non-opioid pain relievers and fever reducers. It has been surprisingly discovered that deuterated forms of acetaminophen may be safely and effectively administered to humans, and other mammals or subjects, for a number of diseases and conditions, including, but not limited to, treatment of pain and fever. It has also been surprisingly discovered that deuterated forms of acetaminophen, such as acetaminophen-d4 (shown below), when administered, unexpectedly form less of the toxic metabolite, NAPQI, and therefore may be used to treat pain and fever while reducing the risk of liver injury and other side effects associated with non-deuterated forms of acetaminophen.

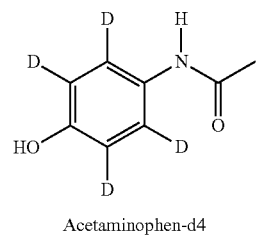

Acetaminophen-d4

In one embodiment, the subject matter disclosed herein provides a pharmaceutical composition comprising a compound of Formula (I):

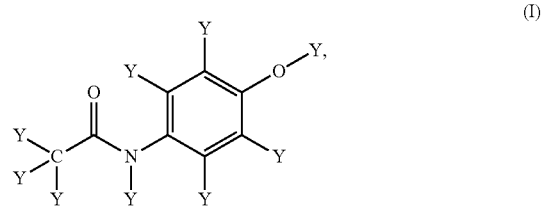

or a pharmaceutically acceptable salt thereof; wherein each Y is independently hydrogen or deuterium; and at least one Y is deuterium.

It has been surprisingly discovered that the replacement of one or more hydrogen atoms with deuterium in a compound of Formula (I) results in a compound with unexpectedly different and superior properties, including avoidance or reduced incidence of life-threatening side effects related to hepatoxicity. These compounds, and compositions comprising them, are useful for preventing or treating a number of conditions, including pain and fever.

BRIEF DESCRIPTION OF THE DRAWINGS

FIG. 1 shows the total amount of GSH conjugates of NAPQI (a marker of NAPQI) formed by acetaminophen-d4 and acetaminophen, respectively.

DETAILED DESCRIPTION OF THE INVENTION

In one embodiment, the subject matter disclosed herein provides a pharmaceutical composition comprising a compound of Formula (I):

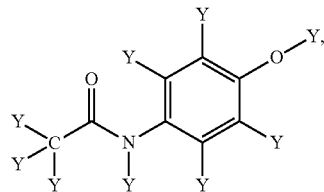
(I)

or a pharmaceutically acceptable salt thereof; wherein each Y is independently hydrogen or deuterium; and at least one Y is deuterium.

In another embodiment, the subject matter disclosed herein provides a pharmaceutical composition comprising a compound of Formula (I):

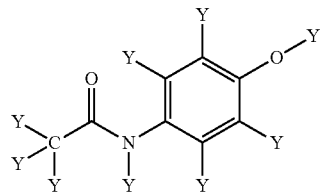
(I)

or a pharmaceutically acceptable salt thereof, wherein at least two, three, four, five, six, seven, eight, or all instances of Y are deuterium.

In a particular embodiment of the compound of Formula (I), or pharmaceutically acceptable salt thereof, one instance of Y is deuterium. In a particular embodiment of the compound of Formula (I), or pharmaceutically acceptable salt thereof, two instances of Y are deuterium. In a particular embodiment of the compound of Formula (I), or pharmaceutically acceptable salt thereof, three instances of Y are deuterium. In a particular embodiment of the compound of Formula (I), or pharmaceutically acceptable salt thereof, four instances of Y are deuterium. In a particular embodiment of the compound of Formula (I), or pharmaceutically acceptable salt thereof, five instances of Y are deuterium. In a particular embodiment of the compound of Formula (I), or pharmaceutically acceptable salt thereof, six instances of Y are deuterium. In a particular embodiment of the compound of Formula (I), or pharmaceutically acceptable salt thereof, seven instances of Y are deuterium. In a particular embodiment of the compound of Formula (I), or pharmaceutically acceptable salt thereof, eight instances of Y are deuterium. In a particular embodiment of the compound of Formula (I), or pharmaceutically acceptable salt thereof, all instances of Y are deuterium.

In certain embodiments, the compound of Formula (I) has a structure selected from:

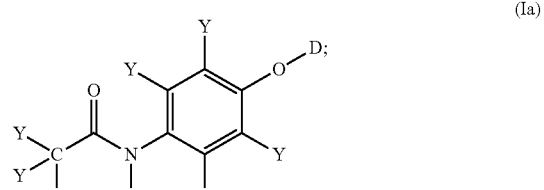
(Ia)

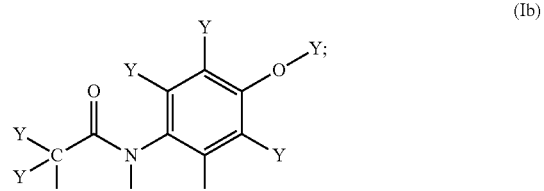
(Ib)

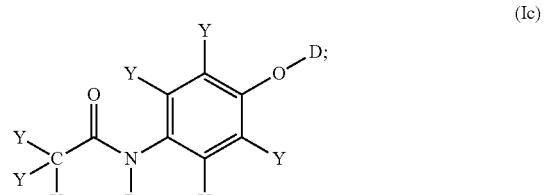
(Ic)

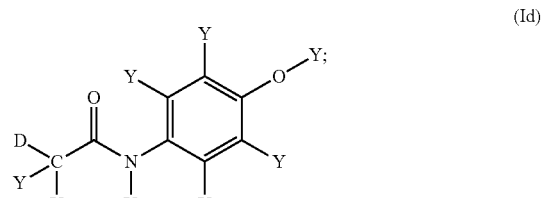
(Id)

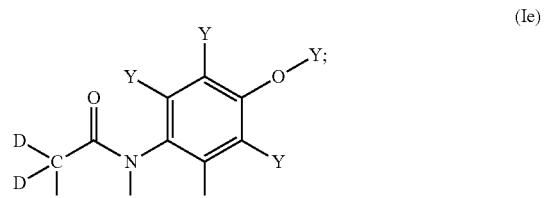
(Ie)

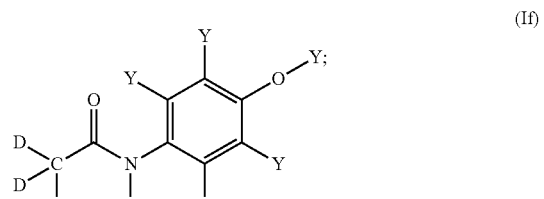
(If)

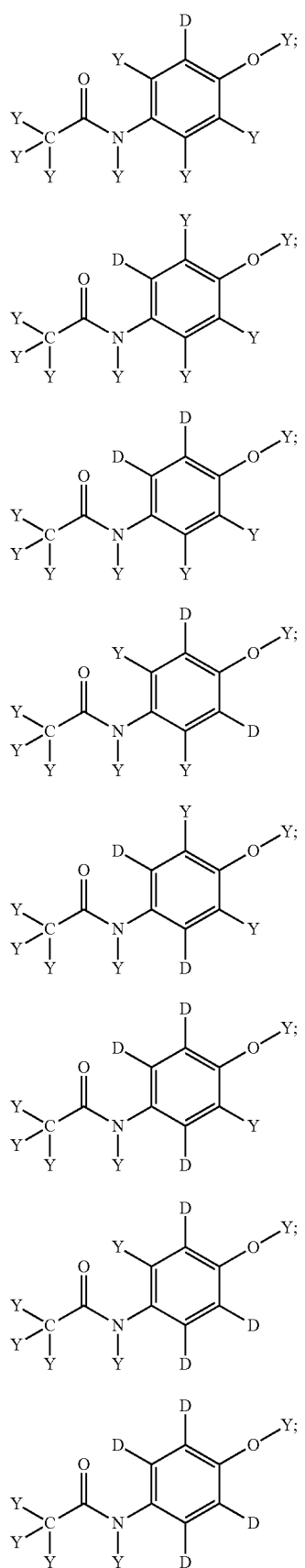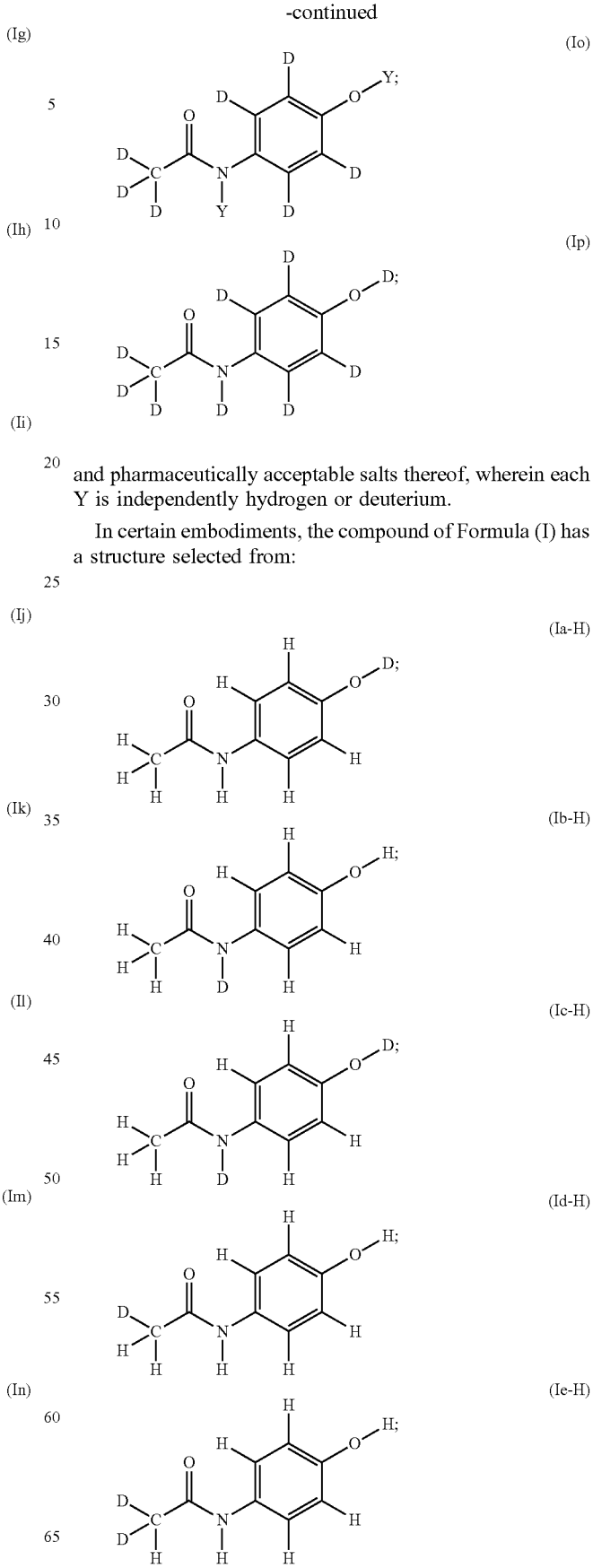
and pharmaceutically acceptable salts thereof, wherein each Y is independently hydrogen or deuterium.
In certain embodiments, the compound of Formula (I) has a structure selected from:

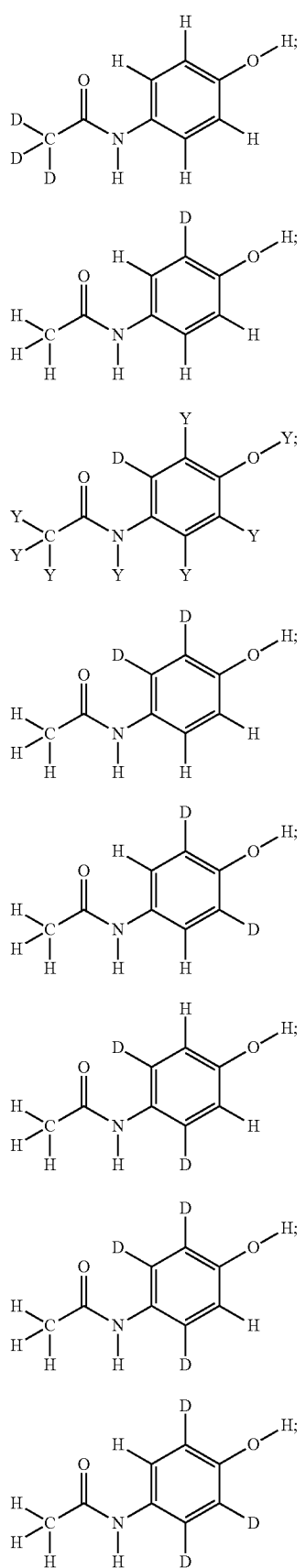

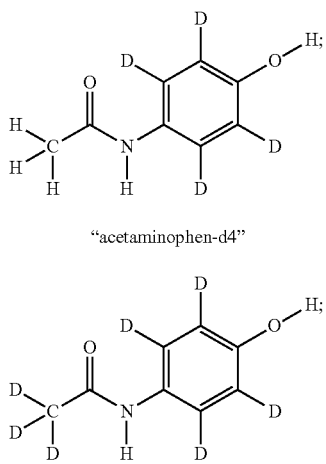

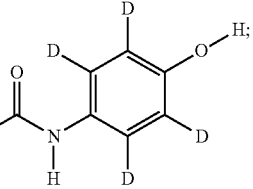

"acetaminophen-d4"

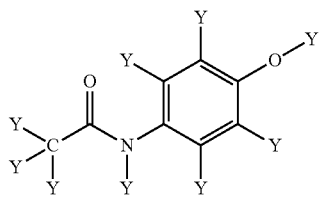

and pharmaceutically acceptable salts thereof.

In a particular embodiment, the compound of Formula (I) is (Ia-H), or a pharmaceutically acceptable salt thereof. In another particular embodiment, the compound of Formula (I) is (Ib-H), or a pharmaceutically acceptable salt thereof. In another particular embodiment, the compound of Formula (I) is (Ic-H), or a pharmaceutically acceptable salt thereof. In another particular embodiment, the compound of Formula (I) is (Id-H), or a pharmaceutically acceptable salt thereof. In another particular embodiment, the compound of Formula (I) is (Ie-H), or a pharmaceutically acceptable salt thereof. In another particular embodiment, the compound of Formula (I) is (If-H), or a pharmaceutically acceptable salt thereof. In another particular embodiment, the compound of Formula (I) is (Ig-H), or a pharmaceutically acceptable salt thereof. In another particular embodiment, the compound of Formula (I) is (Ih-H), or a pharmaceutically acceptable salt thereof. In another particular embodiment, the compound of Formula (I) is (Ii-H), or a pharmaceutically acceptable salt thereof. In another particular embodiment, the compound of Formula (I) is (Ij-H), or a pharmaceutically acceptable salt thereof. In another particular embodiment, the compound of Formula (I) is (Ik-H), or a pharmaceutically acceptable salt thereof. In another particular embodiment, the compound of Formula (I) is (Il-H), or a pharmaceutically acceptable salt thereof. In another particular embodiment, the compound of Formula (I) is (Im-H), or a pharmaceutically acceptable salt thereof. In another particular embodiment, the compound of Formula (I) is (In-H), or a pharmaceutically acceptable salt thereof. In another particular embodiment, the compound of Formula (I) is (Io-H), or a pharmaceutically acceptable salt thereof.

In another embodiment, the subject matter disclosed herein provides a pharmaceutical composition comprising a compound of Formula (I):

or a pharmaceutically acceptable salt thereof, wherein at least one, two, three, or all four instances of Y on the phenyl group are deuterium, and the other instances of Y are hydrogen or deuterium. In one embodiment, the subject matter disclosed herein provides a pharmaceutical composition comprising acetaminophen-d4. In certain embodiments, the deuterated acetaminophen as provided herein has an isotopic purity of at least 90.0%, 95.0%, 97.0%, 98.0%, 99.0%, 99.5%, 99.7%, or 99.9%. In some embodiments, a "compound of Formula (I)" may be considered to indicate more than a single molecule. For example, the compound of Formula (I) may be present in an amount measured in micrograms, milligrams, grams, or kilograms, and as such comprises a large number of individual molecules. For such isotopically-labeled molecules, isotopic enrichment may be described as a percentage indicating the percent of isotopic atoms at a particular site on the molecule. The percentage can be referred to as the "isotopic purity" of the isotopically-labeled compound.

In certain embodiments, the compound of Formula (I), or pharmaceutically acceptable salt thereof, has an isotopic purity of at least 90.0% In certain embodiments, the compound of Formula (I), or pharmaceutically acceptable salt thereof, has an isotopic purity of at least 95.0%. In certain embodiments, the compound of Formula (I), or pharmaceutically acceptable salt thereof, has an isotopic purity of at least 97.0%. In certain embodiments, the compound of Formula (I), or pharmaceutically acceptable salt thereof, has an isotopic purity of at least 98.0%. In certain embodiments, the compound of Formula (I), or pharmaceutically acceptable salt thereof, has an isotopic purity of at least 99.0%. In certain embodiments, the compound of Formula (I), or pharmaceutically acceptable salt thereof, has an isotopic purity of at least 99.5%. In certain embodiments, the compound of Formula (I), or pharmaceutically acceptable salt thereof, has an isotopic purity of at least 99.7%. In certain embodiments, the compound of Formula (I), or pharmaceutically acceptable salt thereof, has an isotopic purity of at least 99.9%.

Compounds of Formula (I), a pharmaceutically acceptable salts thereof, may comprise stable isotopes of carbon, nitrogen, and oxygen in amounts greater than their natural abundance. For example, one or more carbon atoms may be enriched with $^{13}C$ in an amount greater than about 1.1% (e.g., 1.2-1.5%, 1.5-2%, 2-10%, or more than 10%). One or more nitrogen atoms may be enriched with $^{15}N$ in an amount greater than about 0.4% (e.g., 0.5-1%, 1-2%, 2-10%, or greater than 10%). Likewise, one or more oxygen atoms may be enriched with $^{18}O$ in an amount greater than about 0.2% (e.g., 0.20-0.25%, 0.25-0.5%, 0.5-1%, 1-2%, 2-10%, or greater than 10%).

Definitions

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4} alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The terms "treatment," "treat," and "treating" refer to reversing, alleviating, delaying the onset of, or inhibiting the progress of a disease or condition described herein, or to reversing, alleviating, delaying the onset of, or inhibiting the symptoms of a disease or condition described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "administer," "administering," or "administration" refers to implanting, absorbing, ingesting, injecting, inhaling, applying, or otherwise introducing a compound described herein, or a composition thereof, in or on a subject.

The terms "condition," "disease," and "disorder" are used interchangeably.

The term "effective amount," as used herein, refers to a sufficient amount of the active agent (e.g., deuterated acetaminophen) to produce a desired outcome, e.g. The exact amount required will vary from subject to subject, depending on the species, age, general condition of the subject, and the indication.

The phrase "same or equivalent amount," as used herein refers to amounts as measured by mass or by moles, respectively.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal.

Methods of Manufacture

Deuterated acetaminophen as described herein may be prepared by known methods. For example, acetaminophen-d4 may be prepared as described in Johnston et al., Synthesis of acetaminophen-d4, Journal of Labelled Compounds and Radiopharmaceuticals, 25, 12, (1315-1318) (2006) and Freed et al., The synthesis of acetaminophen-d4, Journal of Labelled Compounds and Radiopharmaceuticals, 15, S1 (637-643) (1978), both of which are incorporated by reference herein in their entirety.

Administration and Dosage

In certain embodiments, the pharmaceutical composition comprising a compound of Formula (I), or a pharmaceutically acceptable salt thereof, as described herein, is suitable for oral administration, intravenous (IV) administration, or topical administration. In a particular embodiment, the pharmaceutical composition is suitable for oral administration. In other embodiments, the pharmaceutical composition described herein is in a solid dose form, such as a rapidly disintegrating, immediate, or extended release tablet, caplet, or capsule; oral suspension or syrup; or granule, powder, sachet, or chewable.

In another particular embodiment, the pharmaceutical composition is suitable for intravenous (IV) administration. In certain embodiments, the pharmaceutical composition described herein is in a solution, such as a solution suitable for intravenous (IV) administration.

In another particular embodiment, the pharmaceutical composition is suitable for topical administration. For example, the topical composition may be a cream, foam, gel, lotion, ointment, transdermal patch, tincture, or paste.

In the pharmaceutical compositions described herein, the weight percentage of the compound of Formula (I), or a pharmaceutically acceptable salt thereof, in the total amount of acetaminophen present in the pharmaceutical composition ranges from about 1% to about 100%. In certain embodiments, the weight percentage ranges from about 10% to about 100%. In certain embodiments, the weight percentage ranges from about 10% to about 50%. In certain embodiments, the weight percentage ranges from about 20% to about 100%. In certain embodiments, the weight percentage ranges from about 20% to about 50%. In certain embodiments, the weight percentage ranges from about 30% to about 100%. In certain embodiments, the weight percentage ranges from about 30% to about 50%. In certain embodiments, the weight percentage ranges from about 40% to about 100%. In certain embodiments, the weight percentage ranges from about 40% to about 50%. In certain embodiments, the weight percentage ranges from about 50% to about 100%. In certain embodiments, the weight percentage ranges from about 50% to about 60%. In certain embodiments, the weight percentage ranges from about 60% to about 100%. In certain embodiments, the weight percentage ranges from about 60% to about 70%. In certain embodiments, the weight percentage ranges from about 70% to about 100%. In certain embodiments, the weight percentage ranges from about 70% to about 80%. In certain embodiments, the weight percentage ranges from about 80% to about 100%. In certain embodiments, the weight percentage ranges from about 80% to about 90%. In certain embodiments, the weight percentage ranges from about 90% to about 100%.

In certain embodiments, the pharmaceutical compositions described herein comprise an amount of isotopically-enriched acetaminophen, or a pharmaceutically acceptable salt thereof, wherein the isotopically-enriched acetaminophen comprises a greater percentage of a compound of Formula (I) than that which would occur naturally, e.g., as a result of the natural abundance of deuterium. The natural abundance of deuterium is approximately 0.02% (0.03% by mass). For example, the percentage of a compound of Formula (I) in the acetaminophen may be at least 0.1%, at least 0.5%, at least 1.0, at least 2.0%, at least 3.0%, at least 4.0%, at least 5.0%, at least 10.0%, at least 20.0%, at least 30.0%, at least 40.0%, at least 50.0%, at least 60.0%, at least 70.0%, at least 75.0%, at least 80.0%, at least 85.0%, at least 90.0%, at least 95.0%, at least 97.0%, at least 98.0%, at least 99.0%, at least 99.5%, at least 99.7%, at least 99.8%, at least 99.9%, or at least 100%.

The pharmaceutical compositions described herein may further comprise a pharmaceutically acceptable carrier. In certain embodiments, the pharmaceutical composition as described herein may be formulated (e.g. by using the same excipients) in the same way as commercially available products containing non-deuterated acetaminophen, such as Tylenol-brand products.

As a solid dosage form such as a tablet, caplet, capsule, or chewable, the pharmaceutical composition may comprise at least 40 mg, 80 mg, 160 mg, 325 mg, 500 mg, 650 mg, or 1000 mg of a compound of Formula (I), or a pharmaceutically acceptable salt thereof. In certain embodiments, the pharmaceutical composition comprises about 40-80 mg, about 80 mg-160 mg, about 160 mg-325 mg, or about 325 mg-500 mg of a compound of Formula (I), or a pharmaceutically acceptable salt thereof.

As an oral suspension, the pharmaceutical composition may comprise at least 40 mg, 80 mg, 160 mg, or 325 mg per 5 mL of a compound of Formula (I), or a pharmaceutically acceptable salt thereof. In another aspect, as an oral suspension, the pharmaceutical composition may comprise at least 8 mg, 16 mg, 32 mg, or 65 mg per mL of a compound of Formula (I) or a pharmaceutically acceptable salt thereof. In certain embodiments, 1 mL of the pharmaceutical composition comprises about 8-16 mg, about 16 mg-32 mg, about 32 mg-65 mg, or about 65 mg-100 mg of a compound of Formula (I), or a pharmaceutically acceptable salt thereof. In certain embodiments, 5 mL of the pharmaceutical composition comprises about 40-80 mg, about 80 mg-160 mg, about 160 mg-325 mg, or about 325 mg-500 mg of a compound of Formula (I), or a pharmaceutically acceptable salt thereof.

As a solution for intravenous (IV) administration, the pharmaceutical composition may comprise at least 1 mg, 2 mg, 5 mg, 10 mg, 15 mg, 20 mg, 25 mg or 30 mg per mL of a compound of Formula (I), or a pharmaceutically acceptable salt thereof. In certain embodiments, 1 mL of the pharmaceutical composition comprises about 1-2 mg, about 2 mg-5 mg, about 5 mg-10 mg, about 10 mg-15 mg, about 15 mg-20 mg, about 20 mg-25 mg, or about 25 mg-30 mg of a compound of Formula (I), or a pharmaceutically acceptable salt thereof.

In other embodiments, the pharmaceutical composition may comprise a compound of Formula (I), or a pharmaceutically acceptable salt thereof, as the sole active ingredient, or may be combined in a pharmaceutical composition with one or more other active ingredients (i.e., one or more additional agents), to treat a number of conditions, including as a pain reliever and fever reducer for headaches, muscle aches, arthritis, backache, toothaches, colds, and fevers; or to treat conditions such as allergy, cough, colds, flu, and sleeplessness. Prophylactic, preventative, and palliative uses of the pharmaceutical compositions described herein are within the scope of the invention. Non-limiting examples of active ingredients (i.e., additional agents) with which a compound of Formula (I), or a pharmaceutically acceptable salt thereof, may be combined include: opioids (i.e., opioid analgesics), such as codeine, hydrocodone, oxycodone, tramadol, fentanyl, hydromorphone, meperidine, methadone, or morphine; NSAIDs, such as aspirin , ibuprofen, naproxen, sulindac, ketoprofen, tolmetin, etodolac, fenoprofen, diclofenac, flurbiprofen, piroxicam, ketorolac, indomethacin, nabumetone, oxaprozin, mefanamic acid, or diflunisal; caffeine; antihistamines, such as diphenhydramine hydrochloride; cough suppressants, such as dextromethorphan; expectorants, such as guaifenesin; decongestants, such as phenylephrine hydrochloride; and COX-2 inhibitors such, as rofecoxib, celecoxib, valdecoxib, or etoricoxib. Other examples of additional agents include sleep agents, i.e., agents which decrease the onset time, or which improve the quality or duration of sleep, in a subject. Such sleep agents include zolpidem tartrate, eszopiclone, or the like.

In certain embodiments, the one or more other active ingredients contain at least one deuterium atom. In one embodiment, the pharmaceutical composition comprises a compound of Formula (I), or a pharmaceutically acceptable salt thereof, an NSAID, and caffeine, wherein the NSAID and/or caffeine contain at least one deuterium atom. In another embodiment, the pharmaceutical composition comprises a compound of Formula (I), or a pharmaceutically acceptable salt thereof, and an NSAID, wherein the NSAID contains at least one deuterium atom. In another embodiment, the pharmaceutical composition comprises a compound of Formula (I), or a pharmaceutically acceptable salt thereof, and caffeine, wherein the caffeine contains at least one deuterium atom. In certain particular embodiments, the caffeine is caffeine-d9 (or 1,3,7-tris(trideuteriomethyl)purine-2,6-dione). In certain particular embodiments, the caffeine is caffeine-d10.

Methods and Uses

In another embodiment, a method is provided for treating a disease or condition in a subject, the method comprising administering to the subject a pharmaceutical composition comprising an effective amount of a compound of Formula (I), or a pharmaceutically acceptable salt thereof.

In yet another embodiment, a method is provided for treating a disease or condition in a subject while avoiding one or more side effects associated with administration of a pharmaceutical composition comprising the same or an equivalent amount of non-deuterated acetaminophen, the method comprising administering to the subject a pharmaceutical composition comprising an effective amount of a compound of Formula (I), or a pharmaceutically acceptable salt thereof. In certain embodiments, the one or more side effects include the formation of NAPQI, hepatotoxicity, liver injury, or other liver-related side effects. Additional side effects include nausea, stomach pain, loss of appetite, itching, swelling (e.g., of the face, throat, or tongue), rash, headache, dark urine, clay-colored stools, jaundice, dizziness, and trouble breathing.

In a particular embodiment, provided herein is a method for treating pain or fever in a subject while avoiding one or more side effects associated with the administration of acetaminophen in a non-deuterated form, the method comprising administering to the subject a pharmaceutical composition comprising an effective amount of a compound of Formula (I), or a pharmaceutically acceptable salt thereof. In certain embodiments, the method reduces the level of NAPQI in the subject by at least 5%, 10%, 15%, 25%, 30%, 35%, 40%, 45%, or 50% when compared to the administration of the same or equivalent amount of acetaminophen in a non-deuterated form.

In another embodiment, a method is provided for treating headache or migraine in a subject, the method comprising administering to the subject a pharmaceutical composition comprising an effective amount of a compound of Formula (I), or a pharmaceutically acceptable salt thereof, an NSAID, and caffeine, wherein the NSAID and/or caffeine contain at least one deuterium atom. In certain particular embodiments, the caffeine is caffeine-d9 (or 1,3,7-tris(trideuteriomethyl) purine-2,6-dione). In certain particular embodiments, the caffeine is caffeine-d10.

In another embodiment, a method is provided for treating a disease or condition in a subject, the method comprising administering to the subject an effective amount of a pharmaceutical composition comprising a compound of Formula (I), or a pharmaceutically acceptable salt thereof, wherein the method reduces the production of reactive metabolites of acetaminophen that conjugate with glutathione when compared to the administration of a composition comprising the same or an equivalent amount of acetaminophen in a non-deuterated form. In certain embodiments, the reactive metabolite is NAPQI. In other embodiments, the production of NAPQI, and/or other reactive metabolites of acetaminophen that conjugate with glutathione, are reduced in the subject by at least 5%, 10%, 15%, 20%, 25%, 30%, 35%, 40%, 45%, 50%, or more when compared to the administration of a composition comprising the same or an equivalent amount of acetaminophen in a non-deuterated form. The production of reactive metabolites or NAPQI may be measured (e.g., in the blood) at about 15 minutes, 30 minutes, 60 minutes, 1 hour, 2 hours, 4 hours, or 8 hours after administration of the deuterated acetaminophen described herein or non-deuterated acetaminophen.

In another embodiment, a method is provided for treating a disease or condition in a subject, the method comprising administering to the subject a pharmaceutical composition comprising an effective amount of a compound of Formula (I), or a pharmaceutically acceptable salt thereof, wherein the method reduces the risk of liver injury when compared to the administration of a composition comprising the same or an equivalent amount of acetaminophen in a non-deuterated form. In other embodiments, the method reduces the risk of liver injury by at least 5%, 10%, 15%, 20%, 25%, 30%, 35%, 40%, 45%, 50%, or more.

In another embodiment, a method is provided for treating a disease or condition in a subject, the method comprising administering to the subject a pharmaceutical composition comprising an effective amount of a compound of Formula (I), or a pharmaceutically acceptable salt thereof, wherein the method reduces the risk of liver injury when compared to the administration of a composition comprising the same or an equivalent amount of acetaminophen in a non-deuterated form, as measured by changes in Liver Function Tests (LFTs), including, but not limited to, aspartate transaminase (AST or SGOT), alanine transaminase (ALT or SGPT), gamma-glutamyl transferase (GGT), and alkaline phosphatase (ALP). In other embodiments, the method reduces the risk of liver injury as measured by one or more LFTs by at least 5%, 10%, 15%, 20%, 25%, 30%, 35%, 40%, 45%, or 50%.

In certain embodiments, the maximum daily dose of a compound of Formula (I), or a pharmaceutically acceptable salt thereof, is greater than 4,000 mg per day. In other embodiments, the maximum daily dose of a compound of Formula (I), or a pharmaceutically acceptable salt thereof, is up to 6,000 mg per day. In certain other embodiments, the maximum daily dose of a compound of Formula (I), or a pharmaceutically acceptable salt thereof, is up to 7,000 mg, 8,000 mg, 10,000 mg, or 12,000 mg per day.

In the methods described herein, the compound of Formula (I) has the structure:

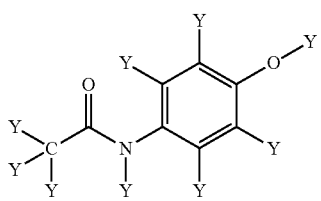

or a pharmaceutically acceptable salt thereof; wherein each Y is independently hydrogen or deuterium; and at least one Y is deuterium.

In certain particular embodiments of the methods described herein, the compound of Formula (I) is compound (Ia), or a pharmaceutically acceptable salt thereof. In certain particular embodiments, the compound of Formula (I) is compound (Ib), or a pharmaceutically acceptable salt thereof. In certain particular embodiments, the compound of Formula (I) is compound (Ic), or a pharmaceutically acceptable salt thereof. In certain particular embodiments, the compound of Formula (I) is compound (Id), or a pharmaceutically acceptable salt thereof. In certain particular embodiments, the compound of Formula (I) is compound (Ie), or a pharmaceutically acceptable salt thereof. In certain particular embodiments, the compound of Formula (I) is compound (If), or a pharmaceutically acceptable salt thereof. In certain particular embodiments, the compound of Formula (I) is compound (Ig), or a pharmaceutically acceptable salt thereof. In certain particular embodiments, the compound of Formula (I) is compound (Ih), or a pharmaceutically acceptable salt thereof. In certain particular embodiments, the compound of Formula (I) is compound (Ii), or a pharmaceutically acceptable salt thereof. In certain particular embodiments, the compound of Formula (I) is compound (Ij), or a pharmaceutically acceptable salt thereof. In certain particular embodiments, the compound of Formula (I) is compound (Ik), or a pharmaceutically acceptable salt thereof. In certain particular embodiments, the compound of Formula (I) is compound (Il), or a pharmaceutically acceptable salt thereof. In certain particular embodiments, the compound of Formula (I) is compound (Im), or a pharmaceutically acceptable salt thereof. In certain particular embodiments, the compound of Formula (I) is compound (In), or a pharmaceutically acceptable salt thereof. In certain particular embodiments, the compound of Formula (I) is compound (Io), or a pharmaceutically acceptable salt thereof. In certain particular embodiments, the compound of Formula (I) is compound (Ip), or a pharmaceutically acceptable salt thereof.

In certain particular embodiments of the methods described herein, the compound of Formula (I) is compound (Ia-H), or a pharmaceutically acceptable salt thereof. In certain particular embodiments, the compound of Formula (I) is compound (Ib-H), or a pharmaceutically acceptable salt thereof. In certain particular embodiments, the compound of Formula (I) is compound (Ic-H), or a pharmaceutically acceptable salt thereof. In certain particular embodiments, the compound of Formula (I) is compound (Id-H), or a pharmaceutically acceptable salt thereof. In certain particular embodiments, the compound of Formula (I) is compound (Ie-H), or a pharmaceutically acceptable salt thereof. In certain particular embodiments, the compound of Formula (I) is compound (If-H), or a pharmaceutically acceptable salt thereof. In certain particular embodiments, the compound of Formula (I) is compound (Ig-H), or a pharmaceutically acceptable salt thereof. In certain particular embodiments, the compound of Formula (I) is compound (Ih-H), or a pharmaceutically acceptable salt thereof. In certain particular embodiments, the compound of Formula (I) is compound (Ii-H), or a pharmaceutically acceptable salt thereof. In certain particular embodiments, the compound of Formula (I) is compound (Ij-H), or a pharmaceutically acceptable salt thereof. In certain particular embodiments, the compound of Formula (I) is compound (Ik-H), or a pharmaceutically acceptable salt thereof. In certain particular embodiments, the compound of Formula (I) is compound (Il-H), or a pharmaceutically acceptable salt thereof. In certain particular embodiments, the compound of Formula (I) is compound (Im-H), or a pharmaceutically acceptable salt thereof. In certain particular embodiments, the compound of Formula (I) is compound (In-H), or a pharmaceutically acceptable salt thereof. In certain particular embodiments, the compound of Formula (I) is compound (Io-H), or a pharmaceutically acceptable salt thereof.

In certain embodiments, the disease or condition is "pain" or "a painful condition." Both terms include neuropathic pain (e.g., peripheral neuropathic pain), central pain, defferentation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, post-operative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the disease or condition is an inflammatory disease. The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes Inflammatory diseases include atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn' s disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes post-surgical inflammation.

In certain embodiments, the disease or condition is an autoimmune disease. An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). Exemplary autoimmune diseases include, but are not limited to, glomerulonephritis, Goodpasture' s syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener' s granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

In certain embodiments, the disease or condition is fever. In certain embodiments, "fever" in a human subject is characterized by a temperature of greater than about 98.6° F., greater than about 99.0° F., greater than about 99.4° F., greater than about 99.8° F., greater than about 100° F., greater than about 100.4° F., or greater than about 100.8° F. In certain embodiments, the temperature of the subject is measured inside the subjects mouth, ear, or rectum, or on the surface of the subject's skin (e.g., on the forehead). Fever can be caused by a wide variety of medical conditions, including bacterial, parasitic, or viral infections, inflammation or an inflammatory disease, or a proliferative disease such as cancer. As such, methods of treating fever in a subject by administering a compound of Formula (I), or a salt thereof, or a pharmaceutical composition comprising the same, comprise partially or completely reducing the fever in the subject.

Kits

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form. In some embodiments, the kit further comprises instructions for use, e.g., instructions for combining the container components, and/or instructions for administering the container components to a subject.

EXAMPLES

Example 1

A study was performed to assess whether a deuterated form of acetaminophen would reduce the production of the reactive metabolite NAPQI when compared to a non-deuterated form of acetaminophen. In the study, acetaminophen and acetaminophen-d4 were incubated with human liver microsomes, with glutathione (GSH) as a trapping agent. The collected samples were analyzed by UPLC/HR-MS to screen and identify the possibly forming trapped reactive metabolites.

Sample type: Pooled liver microsomes
Species: Human (pooled)
Time points: 0, 15, 30, 60, 90 minutes with and without cofactors (all with 2 mM GSH)+60 minutes blank
Concentration: 10 μM
Cofactors: NADPH (2 mM), UDPGA (1 mM), alamethicin 15 μg/ml
Protein content: 1 mg/ml
Replicates: 3
Buffer: phosphate buffer pH 7.4+MgCl2 (2 mM)
Incubation volume: 300 μl; Sampling volume: 40 μl; Quenching: 2-fold volume of 75% acetonitrile
Stock solvent: 50% DMSO (spiking 1/100 to incubation)
Positive control: Clozapine (10 μM) GSH used as 1:1 mixture of stable isotope labeled (15N, 13C2) and non-labeled version.

Acetaminophen-d4 and acetaminophen were purchased from Sigma Aldrich. Each compound was incubated with the liver microsomes as specified above. The incubations were quenched using an equal volume of cold acetonitrile and stored at −20° C. until thawed, centrifuged, and analyzed.

The samples were analyzed by UPLC/PDA with high resolution mass spectrometry (QE-Orbitrap-MS on data dependent MS/MS mode) to monitor formation of GSH-trapped reactive metabolites. The analytical method was optimized by using the parent compounds for optimum chromatographic properties (peak shape, resolution, and retention) and mass spectrometric ionization. Metabolites were screened from the acquired data using software-aided data mining with manual confirmation. The detected metabolites were tentatively identified according to the obtained accurate MS data and fragmentation patterns. Metabolite profiles are expressed as relative peak areas (%) in relation to total combined parent+metabolite LC/MS peak area. The results of the study are shown in FIG. 1. The study demonstrate an unexpected and significant difference in the formation of NAPQI between acetaminophen-d4 and acetaminophen, with acetaminophen-d4 forming approximately 25% less NAPQI when compared to non-deuterated acetaminophen. Thus, deuterated forms of acetaminophen can reduce levels of the reactive metabolite NAPQI that is associated with hepatotoxicity, liver injury, and death.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising," "including," and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

What is claimed is:

1. A method for treating pain or fever in a subject in need thereof, the method comprising administering to the subject a pharmaceutical composition comprising an effective amount of compound (In-H):

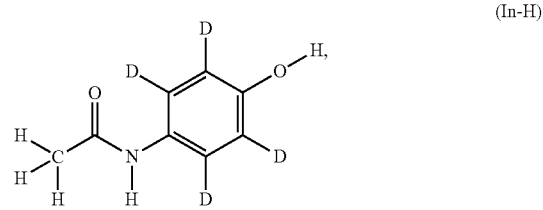

or a pharmaceutically acceptable salt thereof;
wherein the method reduces formation of N-acetyl-p-benzoquinone imine (NAPQI) when compared to the administration of the same or an equivalent amount of acetaminophen in a non-deuterated form.

2. The method of claim 1, wherein the compound, or the pharmaceutically acceptable salt thereof, has an isotopic purity of at least 90.0%.

3. The method of claim 1, wherein the effective amount is between 40-500 mg.

4. The method of claim 1, wherein the pharmaceutical composition comprises at least 40 mg of the compound or the pharmaceutically acceptable salt thereof.

5. The method of claim 1, wherein the pharmaceutical composition is suitable for intravenous (IV) administration.

6. The method of claim 1, wherein the pharmaceutical composition is a solution, syrup, or suspension.

7. The method of claim 1, wherein the pharmaceutical composition is suitable for oral administration.

8. The method of claim 7, wherein the pharmaceutical composition is a solid dose composition.

9. The method of claim 8, wherein the solid dose composition is a tablet, caplet, capsule, granule, powder, sachet, rapidly disintegrating tablet, immediate release tablet, extended-release tablet, or chewable.

10. The method of claim 1, wherein the pharmaceutical composition further comprises one or more additional agents.

11. The method of claim 10, wherein each additional agent is independently an anti-inflammatory agent, opioid analgesic, cough suppressant, antihistamine, decongestant, caffeine, sleep agent, or a combination thereof.

12. The method of claim 1, wherein the method avoids one or more side effects associated with the administration of acetaminophen in a non-deuterated form.

13. The method of claim 12, wherein the side effects are selected from hepatotoxicity and liver injury.

14. The method of claim 12, wherein the side effects are selected from nausea, stomach pain, loss of appetite, itching, swelling, rash, headache, dark urine, clay-colored stools, jaundice, dizziness, or trouble breathing.

15. The method of claim 13, wherein the method reduces the risk of serious liver injury in the subject when compared to the administration of the same or an equivalent amount of acetaminophen in a non-deuterated form.

16. The method of claim 15, wherein the method reduces the risk of serious liver injury as measured by one or more Liver Function Tests (LFTs) in the subject when compared to the administration of the same or an equivalent amount of acetaminophen in a non-deuterated form.

17. The method of claim 16, wherein the method reduces the risk of serious liver injury as measured by one or more LFTs in the subject by at least 5%.

18. The method of claim 16, wherein the LFT is aspartate transaminase, alanine transaminase, gamma-glutamyl transferase, or alkaline phosphatase.

19. The method of claim 1, wherein the method reduces the level of NAPQI in the subject by at least 5% when compared to the administration of the same or an equivalent amount of acetaminophen in a non-deuterated form.

20. The method of claim 1, wherein the maximum daily dose of the compound is up to 6,000 mg, 8,000 mg, or 12,000 mg per day.

21. The method of claim 1, wherein the pain or fever is associated with headache, muscle ache, arthritis, backache, toothache, cold, fever, allergy, cough, flu, or sleeplessness.

22. The method of claim 1, wherein the method is a method of treating pain.

23. The method of claim 1, wherein the method is a method of reducing fever.

24. The method of claim 1, wherein the pharmaceutical composition is suitable for topical administration.

25. The method of claim 24, wherein the topical composition is a cream, foam, gel, lotion, ointment, transdermal patch, tincture, or paste.

26. The method of claim 11, wherein the anti-inflammatory agent is a cyclooxygenase-2 (COX-2) inhibitor.

27. The method of claim 11, wherein the anti-inflammatory agent is an NSAID.

28. The method of claim 1, wherein the pharmaceutical composition comprises a pharmaceutically acceptable carrier.

* * * * *